(12) United States Patent
Park et al.

(10) Patent No.: US 12,232,463 B2
(45) Date of Patent: Feb. 25, 2025

(54) AUTOMATED MICROPROPAGATION SYSTEM FOR PLANT TISSUE CULTURE

(71) Applicants: Jung Wook Park, Surrey (CA); Tien Jung Lee, Surrey (CA); Sayed Md Zobayed, Langley (CA); Flavio Firmani Tulli, Victoria (CA); Jagjit Singh Aujla, Abbotsford (CA)

(72) Inventors: Jung Wook Park, Surrey (CA); Tien Jung Lee, Surrey (CA); Sayed Md Zobayed, Langley (CA); Flavio Firmani Tulli, Victoria (CA); Jagjit Singh Aujla, Abbotsford (CA)

(73) Assignee: JUNG WOOK PARK ET AL., Surrey (CA)

( * ) Notice: Subject to any disclaimer, the term of this patent is extended or adjusted under 35 U.S.C. 154(b) by 764 days.

(21) Appl. No.: 17/430,261

(22) PCT Filed: Mar. 18, 2020

(86) PCT No.: PCT/CA2020/050357
§ 371 (c)(1),
(2) Date: Aug. 11, 2021

(87) PCT Pub. No.: WO2020/186352
PCT Pub. Date: Sep. 24, 2020

(65) Prior Publication Data
US 2022/0124997 A1   Apr. 28, 2022

Related U.S. Application Data

(60) Provisional application No. 62/820,229, filed on Mar. 18, 2019.

(51) Int. Cl.
*C12M 3/00* (2006.01)
*A01G 9/029* (2018.01)
*A01H 4/00* (2006.01)

(52) U.S. Cl.
CPC ........... *A01H 4/001* (2013.01); *A01G 9/0293* (2018.02); *A01H 4/005* (2013.01)

(58) Field of Classification Search
CPC ............................... A01H 4/003; A01H 4/005
See application file for complete search history.

(56) References Cited

U.S. PATENT DOCUMENTS

| | | | | |
|---|---|---|---|---|
| 5,382,268 A * | 1/1995 | Brown | ................... | A01H 4/003 47/1.01 R |
| 5,525,505 A * | 6/1996 | Young | ................... | A01H 4/005 47/60 |

(Continued)

OTHER PUBLICATIONS

Lee et al., A novel automated transplanting system for plant tissue culture. Biosystems Engineering, 2019, vol. 181, pp. 63-72.*

(Continued)

*Primary Examiner* — Nathan A Bowers

(57) ABSTRACT

Examples of an automated micropropagation system for plant tissue culture is provided. The system comprises a culture vessel that comprises a number of detachable culture items that are designed with a plurality of culture cells sized to accept a single plantlet. Such culture vessel is fed into the system to an automated gripper and cutter assembly that is configured to grip the plantlets, cut them and transfer them into a new culture vessel.

13 Claims, 7 Drawing Sheets

(56) References Cited

U.S. PATENT DOCUMENTS

| | | | | |
|---|---|---|---|---|
| 10,830,671 | B2* | 11/2020 | Sercel | G01N 35/00732 |
| 11,140,840 | B2* | 10/2021 | Adelberg | A01H 4/001 |
| 2010/0293850 | A1* | 11/2010 | Fisher | A01G 9/08 47/73 |
| 2019/0183078 | A1* | 6/2019 | Von Rundstedt | A01G 9/086 |
| 2021/0148830 | A1* | 5/2021 | Brown | G01N 35/04 |
| 2021/0204490 | A1* | 7/2021 | Bartrom | A01G 9/042 |
| 2023/0026903 | A1* | 1/2023 | Kendall | A01G 31/06 |

OTHER PUBLICATIONS

International Search Report in International Application No. PCT/CA2020/050357 issued Jun. 18, 2020.

Written opinion on Patentability of International Application No. PCT/CA2020/050357 issued Jun. 18, 2020.

* cited by examiner

FIG. 1- PRIOR ART

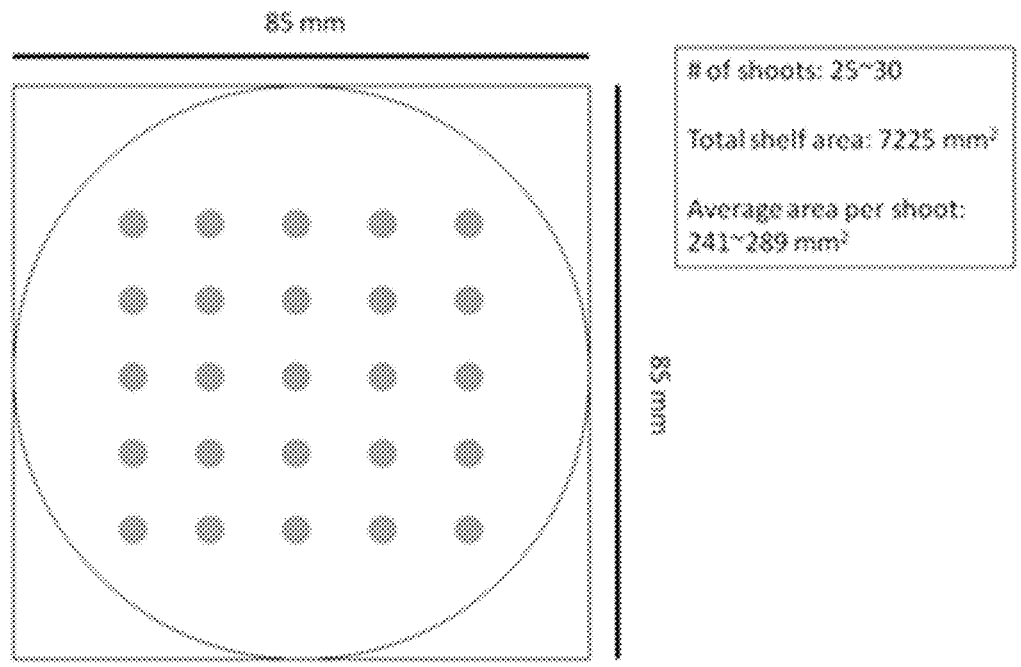
FIG. 4A- PRIOR ART
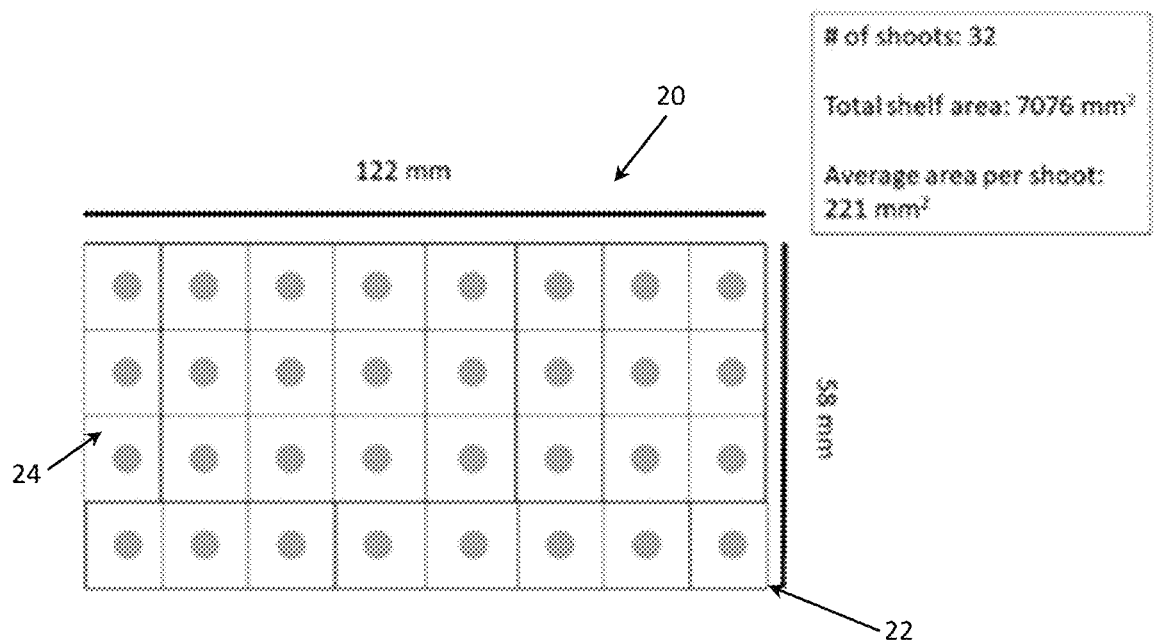
FIG. 4B

AUTOMATED MICROPROPAGATION SYSTEM FOR PLANT TISSUE CULTURE

CROSS REFERENCE TO RELATED APPLICATIONS

This application is a U.S. National Stage Application of International application No. PCT/CA2020/050357 filed Mar. 18, 2020, which claims priority from U.S. Patent Application No. 62/820,229 filed on Mar. 18, 2019. The entirety of all the above-listed applications are incorporated herein by their reference.

FIELD OF INVENTION

This invention relates to a system for transplanting plant tissue culture and more particularly to an automated micropropagation system for plant tissue culture.

BACKGROUND OF INVENTION

Unless otherwise indicated herein, the materials described in this section are not prior art to the claims in this application and are not admitted to be prior art by inclusion in this section.

Micropropagation is a tissue culture technique for cloning and rapid multiplication of genetically homogenous plants. This technique is widely used to propagate high quality and disease-free plants in a short period of time. Micropropagation has become more and more popular because of the increasing demand in agricultural and horticultural products such as berries, potatoes, and orchids. FIG. 1 illustrates a container filled with plantlets that is used in some traditional systems for micropropagation. Traditionally the plantlets are grown in a container 10 filled with a sterile medium 12 containing necessary nutrients, carbohydrates and growth regulators. Under a laminar flow hood, the operator removes the plantlets 14 from the growing medium 12 one by one and cut them into two or three smaller micro-shoots. They are then planted into a new container containing fresh medium and incubated in a controlled environment until they are ready for next transfer. This traditional process is tedious and labour intensive, therefore limiting the application of this technology in some areas due to the high labour cost.

There were many attempts and research conducted by several research groups and companies to automate the micropropagation process; however, they are either inefficient or expensive to implement because of its sophisticated features. Another limiting factor was that every plant varies in different ways so the automated systems designed for specific category of plants may not work properly with different species.

SUMMARY OF THE INVENTION

In one aspect, an automated micropropagation system for plant tissue culture to rapidly produce genetically identical plantlets is provided. The system comprises a culture vessel with a number of detachable vessel vectors (DVVs) where each DVV comprises a plurality of individual and separated culture cells configured and sized to accept at least one plantlet per cell. Some of the DVVs are mother DVVs comprising at least one mother plantlet in each cells and some of the DVVs are new DVVs where each of the cells is filled with a growing medium; A plantlet feed-in assembly has a first feed-in driver that is in communication with at least one mother DVV comprising at least one mother plantlet in each cells of the mother DVV and a second feed-in driver that is in communication with the new DVV. A motorized gripper and cutter assembly is also provided with a gripper, a cutter and a driver that drives the gripper and the cutter in horizontal and vertical directions. The gripper has a number of holders in communication with a holders' driver that drives the holders between a closed position and an opened position. When the holders are in closed position, they hold an array of the plantlets simultaneously. The cutter comprises a number of shears in communication with a shears' driver configured to cut the gripped plantlets to a predetermined length. The driver of the gripper and cutter assembly is configured to move the gripper to transplant the cut part of the plantlets into the new DVV. The new DVVs containing the transplanted parts are collected in a collector assembly that is in communication with the gripper and cutter assembly. A controller is further provided to control the operation of the system. The controller is in communication with the first and the second feed-in drivers, the gripper and cutter assembly's driver, the holders' driver and the shears' driver to control the trigger time of each of the drivers independently.

In another aspect, an automated micropropagation process using an automated micropropagation system is provided. The process comprises providing a set of predetermined parameters by an operator, calculating micropropagation parameters by a controller, providing mother plantlets into a number of detachable vessel vectors (DVVs) where each DVV comprises a plurality of individual culture cells that contain a culture medium. Each culture cell comprises at least one mother plantlet. The process further comprises determining if the length of each plantlets is matching a predetermined length. When the length of the plantlet matches the predetermined length driving the DVV with the mother plantlets in a gripper and cutter assembly where a gripper holds each plantlet in the culture cells separately while a cutter cuts each plantlets at a predetermined position. The dissected part of the plantlets is then transplanted into a new DVV filed with a new culture medium.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

FIG. 4A—PRIOR ART, is a top view of an examples of culture vessels used in known prior art culture vessel.

FIG. 4B is a top view of an example of a culture vessel with an array of detachable vessel vectors (DVVs).

DETAILED DESCRIPTION OF SPECIFIC EMBODIMENTS

Plant tissue culture is advantageous to growers because the overwhelming number of disease-free plants can be produced using the tissue collected from a single parent plant—a plant which itself remains unharmed in the tissue harvesting process. Propagation through tissue culture also eliminates the possibility of any interruption in the growing season because it can be carried out inside a carefully regulated, controlled environment. Since the micropropagation process is highly repetitive and tedious, it becomes a good candidate for automation. In addition, more systematic and consistent production, and better control of the products can be achieved by automating the process of micropropagation.

The system for automated micropropagation of the present invention uses uniquely designed culture vessels that provide easy access to the plantlets and process them in a batch in an upright position rather than taking the shoots out and process them one by one. The automated micropropagation system can be used for a number of plant tissue cultures. For example, the automated micropropagation system has been tested to increase the production rate of *Vaccinium corymbosum* 'Biloxi' blueberry plantlets.

Traditionally, in the field of plant tissue culture, autoclavable polypropylene or polycarbonate containers such as Magenta boxes or a small glass jars are commonly used; however, such containers/jars have a common problem such as shoots getting easily entangled due to their non-discrete placements inside the round jars which may result in a non-uniform plant production. Another problem is that the storage space is not properly utilized due to the empty space between the adjacent jars.

Figure 1:
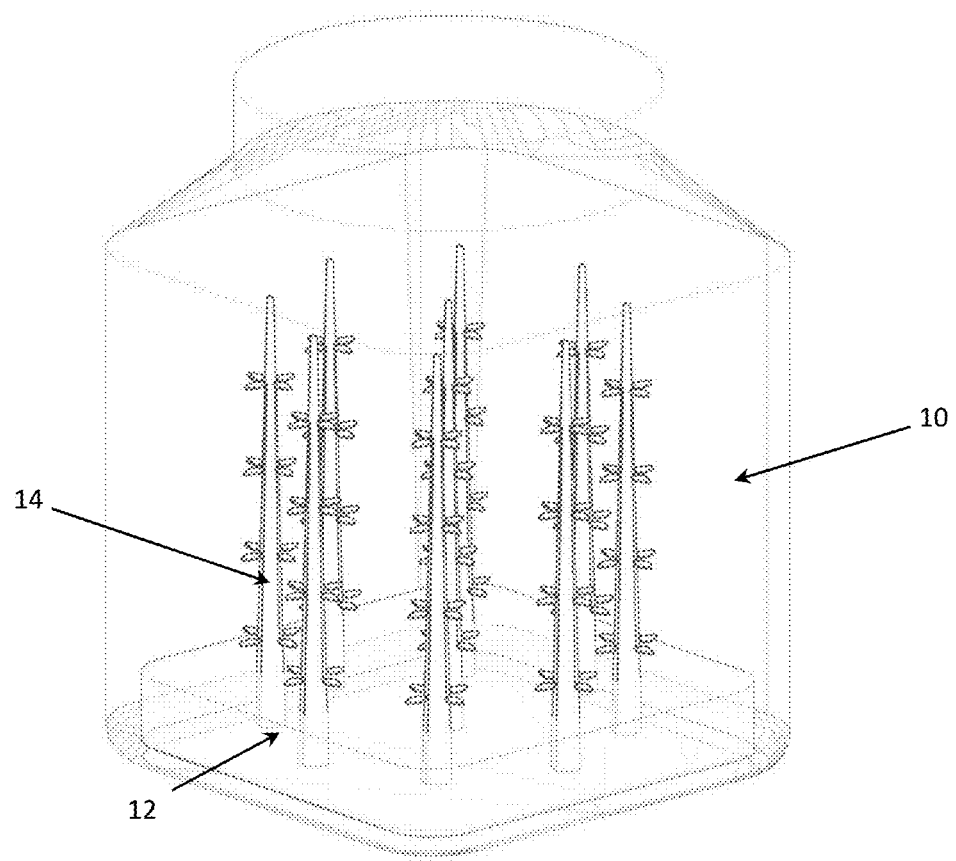
FIG. 1—PRIOR ART, is an environmental view of a storage jar traditionally used for growing micro-propagated plantlets.
Figure 2:
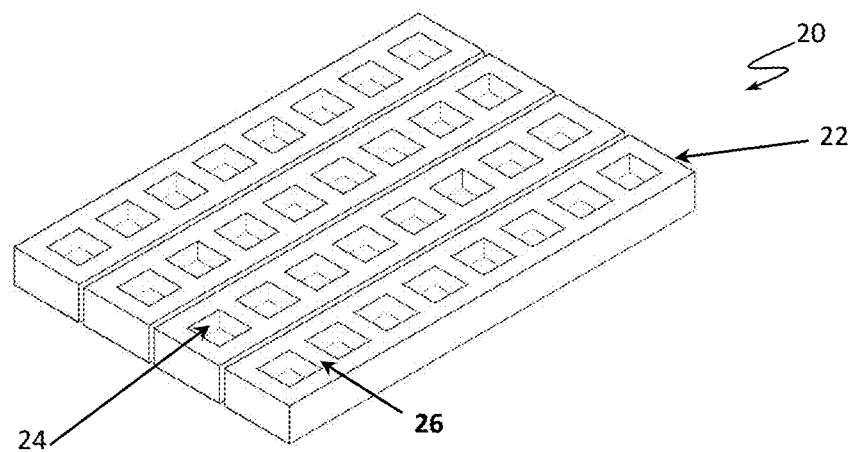
FIG. 2 is a perspective view of an example of a culture vessel used in one embodiment of an automated micropropagation system for plant tissue culture.
Figure 3:
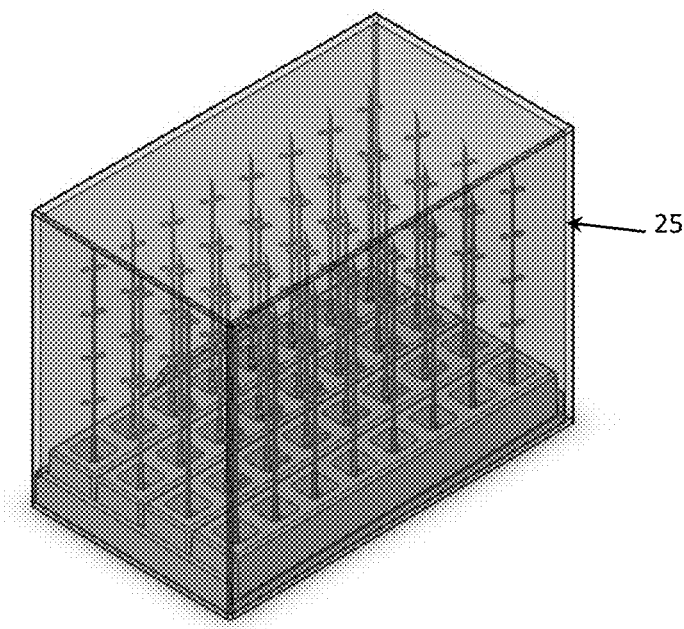
FIG. 3 is a perspective view of a storage container with an array of detachable vessel vectors (DVVs) enclosed with a sterilized snap on transparent cover.

FIG. 2 illustrates a culture vessel 20 that can be used in the system for micropropagation of the present invention. The vessel 20 comprises a number of detachable rows named "Detachable Vessel Vector" or "DVV" 22 that includes a number of individual cells 24 separated one from another. Thus, the system of the present invention utilizes a tray-stacking method for storage. The culture vessel 20 comprises an array of the DVVs 22 that can be easily sterilized after each use. In the illustrated example, each of the DVV 22 is a column with a number of individual cells 24. An array of such columns 22 form the culture vessel 20 and each DVV 22 of the vessel 20 can detach from the rest of the DVVs 22. Each cell 24 of the DVVs 22 is dimensionally optimized to accept a single plantlet, therefore the access to the plantlets is increased and the planting area for storage is optimized. For example, FIG. 4A shows a top view of a culture vessel of a system known in the prior art (e.g., a traditional storage jar), while FIG. 4B shows a top view is the culture vessel 20 of the present invention. As can be seen the storage space for plantlets using traditional storage jar, in the particular example jar, can be approximately 85 mm in diameter, which requires a shelf area of about 7225 $mm^2$. When four DVVs 22 are grouped together and enclosed using a snap on transparent cover 25 as illustrated in FIG. 3, they can occupy a comparable shelf area of about 7076 $mm^2$. In addition, the number of shoots in the traditional storage jar can be approximately 25 to 30 shoots which makes the average area per shoot of about 241-289 $mm^2$, while in the culture vessel 20 the number of shoots can be about 32 shoots which makes the average area per shoot of about 221 $mm^2$. This is for illustration purposes only and the persons skilled in the art would understand that the number of the DVVs 22 in the culture vessel 20 or the number of cells 24 in each DVV and thus the number of shoots in the vessel 20 can be more or less than the illustrated without departing from the scope of the invention.

Each cell 24 is dimensioned and optimized to accept a single plantlet. For example, each cell 24 can be 10×10 mm and a separation wall 26 thickness between each cell can be 2 mm. This is for illustration purposes only and the persons skilled in the art would understand that the cells 24 can have larger or smaller dimensions and the separation wall 26 can be thinner or thicker without departing of the scope of the invention. Using the traditional jars, in the case of blueberry shoots, one storage jar 10 on average can store around 25 to 30 blueberry shoots. Even with 30 shoots in a jar, the average area a shoot takes is around 4% more than that of the storage of a single cell 24.

Figure 5A:
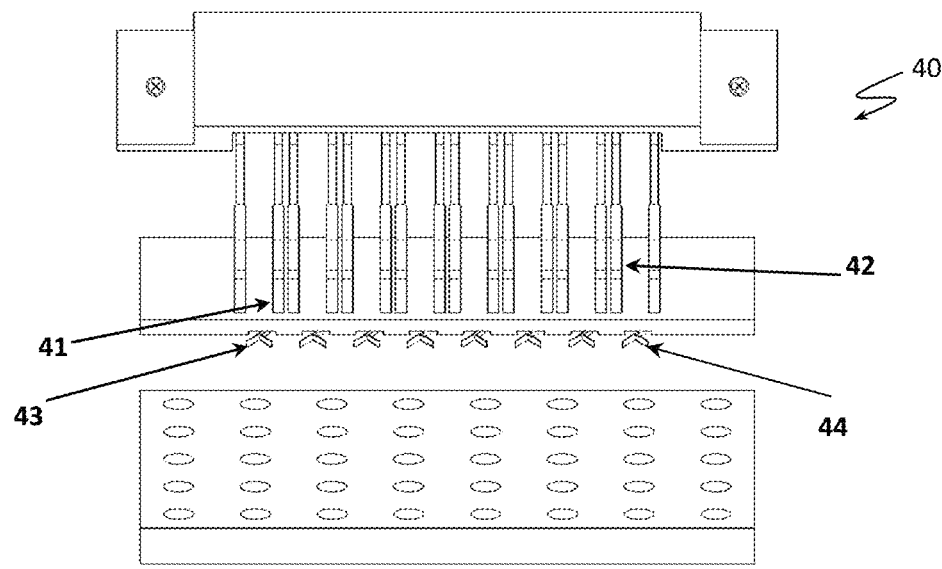
FIG. 5A is an environmental view of a gripper and cutter component of an example of an automated micropropagation system for plant tissue culture.

In any of the known prior automated systems a major drawback was that the nodal segments, which contain the meristem, had to be picked up by a robot which requires a machine vision system that identifies the position and orientation of the shoot on the worktable or conveyor belt. Many plants, including blueberry plantlets by nature grow vertically, in the same direction in which the nodal segments have to be transplanted. In the micropropagation system of the present invention, the plantlets are dissected transversally (micro-shoots remain vertically), without any vision system, and the nodal segments are held in the natural position before transplanting to the sterilized DVVs 22. One advantage of dissecting the plantlets while they are in the DVVs 22 is that it reduces the processing time by skipping the step where the plants are taken out by a manipulator to be dissected. The automated micropropagation system of the present invention includes a specially designed gripper and cutter assembly 40 shown in FIGS. 5A and 5B. The gripper and cutter assembly 40 is used to hold and dissect the shoots and can be designed as a modular assembly, meaning that the component 40 can be customized for different sizes of species by replacing the gripper and cutter assembly. The gripper and cutter assembly 40 comprises a gripper 42, a cutter 44 and an assembly driver (e.g. a solenoid) that drives the gripper and cutter assembly 40 back and forward in Y-direction as well as up and down in Z-direction. Persons skilled in the art would understand that the assembly driver can move the gripper and cutter assembly in X and Z directions without departing from the scope of the invention. In one implementation, the gripper 42 and the cutter 44 can move in horizontal (X or Y) direction and/or in vertical (Z) direction independently one from another. The gripper 42 can comprise a plurality of holders and a driver 48 (see FIG. 5B) that drives each of the holders between a close and open positions. The gripper 42 is configured to hold the plantlets 45 in position, when the holders are closed, so that the plantlets 45 are ready to be dissected (see FIG. 5B). For example, the holders can be a plurality of pair of fingers 41 that are in communication to the driver 48, e.g., a solenoid, so that when the solenoid is energized the fingers travel some pre-determined distance closer to each other (in closed position) to securely hold the plantlet 45. The cutter 44 has a plurality of shears 43 configured to dissect the plantlets 45 into small shoots ready to be planted into new culture vessel 20.

In one embodiment the driver 48 of the holders 41 and the driver of the shears 43 can be in communication with a controller (not shown) that triggers the drivers. When the controller activates the holders' driver (e.g., the solenoid), each of the pair of fingers meet each other in the middle of the opening gap, i.e. the fingers travel toward each other by the same distance to ensure some predefined distance between the fingers. The space between the fingers of each holder 41 is defined by the size of the plantlet 45. The number of the holders 41 as well as the number of shears 43 in the gripper and cutter assembly 40 depends and matches the number of cells 24 in the DVVs 22 which corresponds to the number of plantlets 45.

It is advantageous to have the production of micropropagated shoots increased by multiplying plantlets simultaneously by using the culture vessels 20 where the plantlets 45 can be dissected simultaneously. For example, the gripper 42 will get a hold of a row of plantlets 45 while the cutter 44 dissects the upper part of all the plantlets simultaneously. The gripper 42 hold dissected the nodal segments and will travel to the new DVV to transplant the nodal segments therein, all at once.

Figure 6:
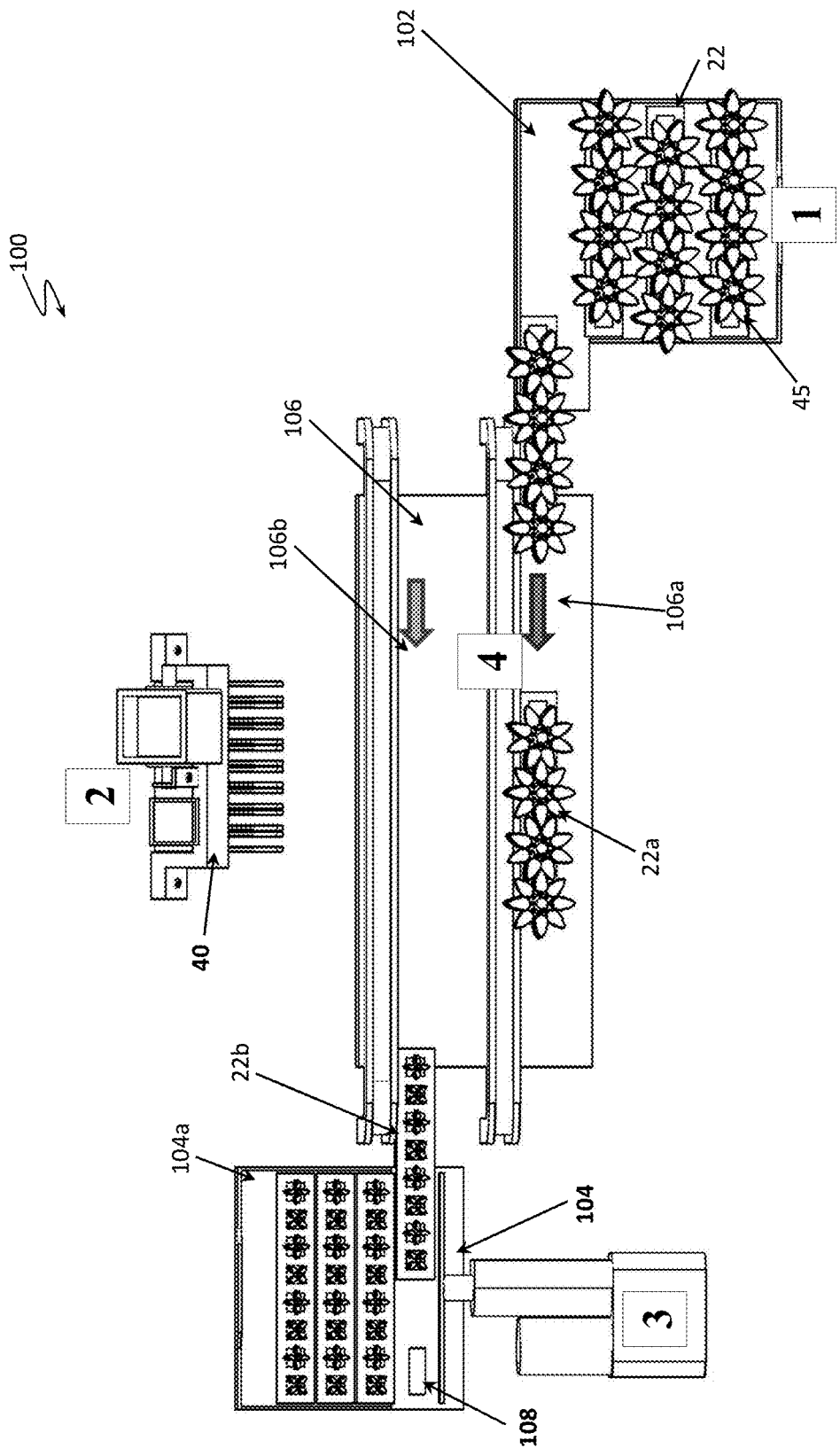
FIG. 6 is a top view of an example of an automated transplanting system for plant tissue culture.

An automated micropropagation system 100 is shown in FIG. 6. The system 100 can comprise a feed-in assembly 102, the gripper and cutter assembly 40, and a collector assembly 104. The feed-in assembly 102 is where the plantlets 45 and the empty DVVs 22 are fed in. Two assembly drivers 106 are used to transport and introduce the DVVs 22 that contains the plantlets 45 into the system 100. Before the process starts, the array of DVVs 22 that contains the mother plantlets 45 are loaded onto the system 100 by a human operator and a push plate is used to push the "old" DVV 22a onto the first assembly driver 106a one by one as illustrated in FIG. 6. The operator will visually inspect the mother DVVs 22 and remove any batch that shows signs of contamination. On the other hand, a second assembly driver 106b will bring in the "new" sterilized destination DVV 22b with fresh medium and position them on the desired position parallel to the mother DVV 22a. When the first assembly driver 106a brings the mother DVV 22a into the gripper and cutter assembly 40, it holds the plantlets 45 and cut them at the predetermined length and then the gripper carries them into the new DVV 22b with the fresh medium. The second driver 106b brings such new DVVs 22b into the collector 104 and a sensor 108 detects arrival of a newly planted DVV 22. For example, the first and/or the second feed-in assembly drivers 106 can each comprise a motor in communication with a conveyor belt.

Some parameters, such as the length of the plantlets 45 and the segmentation length, is required to be set before the automation process starts. The system 100 is designed to adapt different type of plantlets 45. With different type of plantlets 45, the distance between the meristem is different, and thus the segmentation length varies. A cutting profile can be saved for easy access to the parameters when the same type of plants is processed in the future. Without a vision system, these parameters become important as, for example, the segmentation length specifies the length to be cut to ensure that there is at least one meristem in each segment. The length of the plantlets 45 is then used to calculate the number of cuts needed.

Figure 5B:
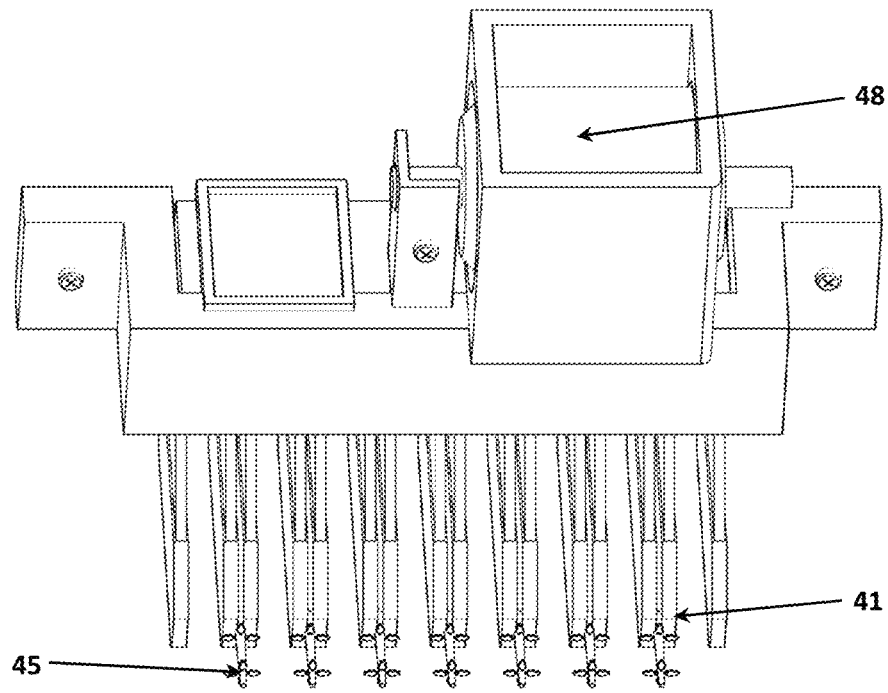
FIG. 5B is an environmental view of the gripper and cutter component of FIG. 4A during cutting operation.

The system 100 can use three drivers, e.g., three stepper motors, to move the three linear stages accordingly. For example, one linear stage is used to move the gripper and the cutter assembly 40 in the up and down (Z) direction, while the other two linear stages are used to move the gripper 42 and the cutter 44 back and forth (Y) direction, respectively, between the mother DVV 22a and the new DVV 22b. Two solenoids are used to activate the holders 41 and the shears 43, respectively. FIG. 5B shows the holders 41 gripping the plantlets 45 and the shears 43 in action. The holders 41 can hold the plantlets 45 in position so the plantlets 45 are ready to be dissected by the shears 43.

The system 100 can further comprise a controller (not shown) that is in communication with the first and second feed-in drivers 106a and 106b, the gripper and cutter assembly's driver (not shown), the holders' driver (e.g., the solenoid) and the shears' driver so that it controls the triggering time of each of the drivers independently. In one implementation, a plurality of sensors can be provided to provide input signals to the controller. For example, when the mother DVV and the new DVV are loaded into the feed-in assembly 102 the sensor sends an input signal to the feed-in drivers 106a, 106b to bring the respective DVVs in the gripper and cutter assembly 40. When the mother and the new DVVs are in the pre-determined position, parallel one to the other, a position sensor can send a signal to the controller to trigger the driver of the gripper and cutter assembly to position it into the predetermined position in proximity to the mother DVV and to close each of the pair of fingers 41 around each of the plantlets 45 and cut a part (nodal segment) of the plantlets 45. Then the controller triggers the driver of the gripper and cutter assembly to move the gripper 42 to the new DVV 2b and transplant the dissected part into the cells of the new DVVs.

After the automation process is finished, the DVV 22b, in which the shoots are planted, are transported to the collector 104 by the second driver 106b. The collector 104 collects the new DVVs 22b and stack them together one by one. The collector 104 consists of a base to mount a collector tray 104a, a push plate activated by a linear actuator, and a light sensor 108 that detects the new DVVs 22b arrival. When the light sensor is covered by the incoming DVV 22b the linear actuator is activated and push such DVV 22b into the collector tray 104a. After the DVVs 22 are stacked together, the operator covers it with the sterilized snap on transparent cover 25 (see FIG. 3), wraps with plastic wrap, and transports it to the storage room.

Figure 7:
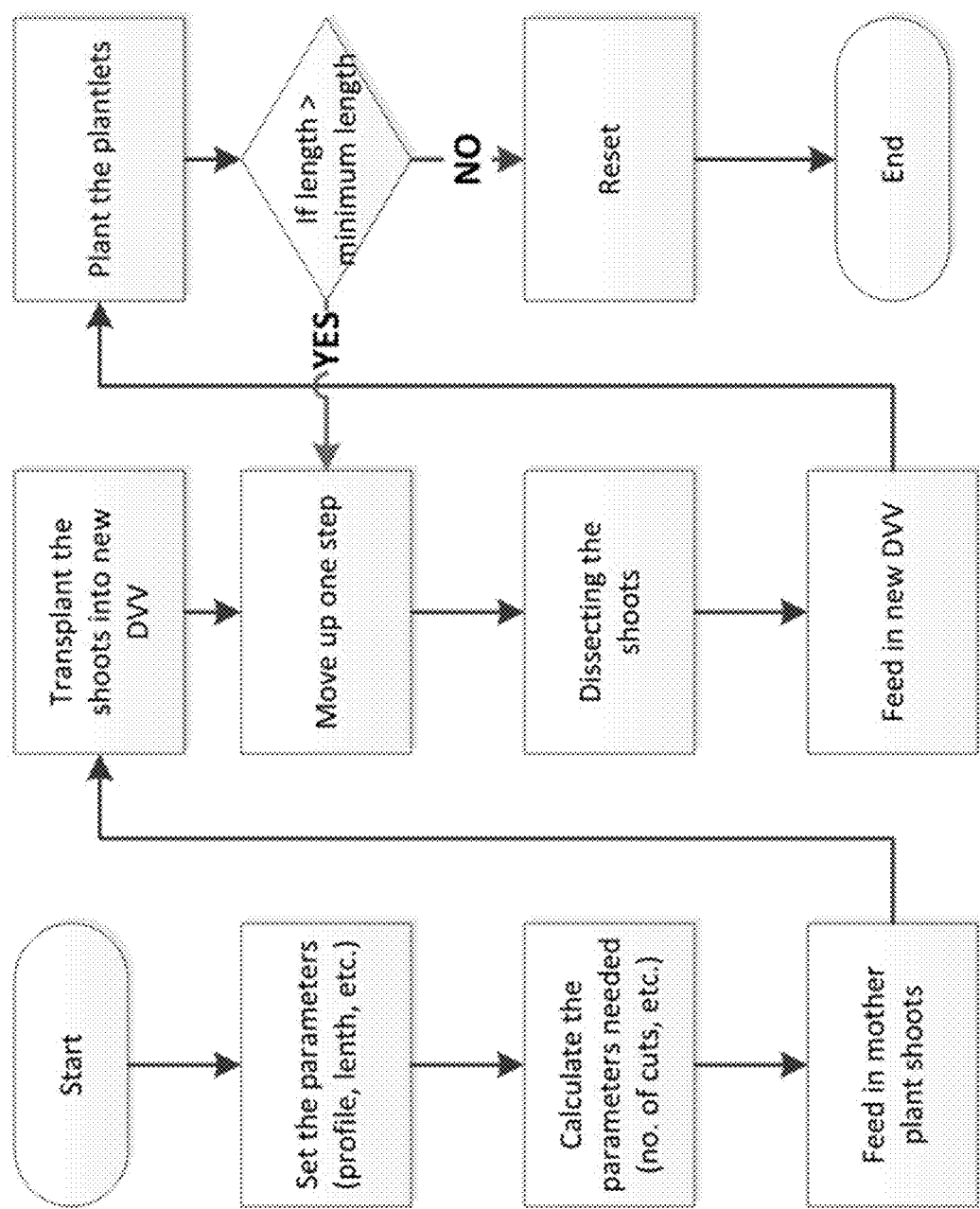
FIG. 7 is a flowchart of an example of an automated micropropagation process of the present invention.

FIG. 7 illustrates a flowchart of one mode of operation of the automated micropropagation system 100. First, the operator sets up the parameters, such as for example, the length of the plantlets 45, then the system calculates the parameters needed, such as for example, the number of cuts based on the set-up parameters and the particular plant. Then the mother plantlets DVV are fed into the feed-in assembly 102 of system 100 and pushed into the gripper and cutter assembly 40 of the system 100 where they are cut and transplanted into new DVVs 22b. The system 100 can resets when the mother plantlets reach a minimum length or the number of the pre-determined cuts is reached, for example, depending on the chosen mode of operation.

To demonstrate the feasibility of the proposed system 100, pilot experimental tests were conducted in a laboratory setting. One variety of the blueberry plants, the tetraploid southern highbush 'Biloxi', was used in the tests. Tetraploid southern highbush Biloxi plants are upright with an average mature height of between 1.5 to 1.8 meters. Before each trial run, the plantlets were transferred from the storage jars to the DVVs manually. The DVVs were filled with the gel-like growing medium (solidified by using Gellan Gum) to hold the shoots in position. Thirteen pilot trials were carried out to test the success rate and efficiency of the system for the Biloxi plantlets. For each trial, the numbers of cuts were specified between 2-4 cuts in relation to the length of the plantlets. The empty DVVs were loaded to the system by the operator through the assembly belt. The testing protocols were as follow: 1) 8 shoots planted in a DVV for 2 cuts; 2) 8 shoots planted in a DVVs for 3 cuts; and 3) 8 shoots planted in a DVV for 4 cuts. The only variable between the tests was the number of cuts executed on the plantlets. The purpose of the tests is to observe the overall performance, i.e. the success rate and efficiency, of the machine as the number of executed cuts increased. In total, 104 plantlets were used to derive the success rate and the efficiency, which are defined, respectively, as follows:

success rate=$O_S/O_T$ [%], where $O_S$ is the total number of the successfully planted micro-shoots and $O_T$ is the number of total processed micro-shoots.

efficiency=$O_S/T$ [shoots/hour], where T is the time it takes to successfully plant $O_S$ micro-shoots by the system in an hour. By definition, a micro-shoot is successfully planted when it stays in the DVV and has at least more than one nodal segment or shoot tip. Without the nodal segment or shoot tip the plantlet will not survive. As a result, it is not counted toward the successfully planted micro-shoots. $O_T$ is calculated based on the number of plantlets and the number of cuts performed.

Three test protocols were carried out as described in the previous section and the test results are tabulated in Table I. From the results, the success rate was close to 90% with 2 cuts, while with 3 cuts and with 4 cuts were around 80% and 72%, respectively. In addition, the efficiency with 2 cuts was around 674 shoots per hour while with 3 cuts and 4 cuts were 711 shoots per hour and 694 shoots per hour, respectively. Table II shows the error sources for the 2-Cuts, 3-Cuts and 4-Cuts settings. There are two main error sources: 1) gripping error: unsuccessfully gripped plantlets, and 2) cutting error: unsuccessfully cut plantlets. For the 2-Cuts setting, the gripping error was around 7.7% of what the supposed outcome would be, while the cutting error was around 1.0%. On the other hand, the gripping error and the cutting error of the 3-Cuts setting were 13.0% and 2.2%, respectively. In addition, the 4-Cuts setting exhibited 14.1% gripping error and 1.6% cutting error.

TABLE I

THE TEST RESULTS OF THE AUTOMATED MICROPROPAGATION SYSTEM FOR VACCINIUM CORYMBOSUM - 'BILOXI' WITH 2 CUTS, 3 CUTS, AND 4 CUTS.

| | Test No. | No. of Available Shoots | Time [s] | No. of Successful Transplants | No of Ideal Transplants | Efficiency [shoots/hr] | Success Rate |
|---|---|---|---|---|---|---|---|
| 2-Cuts | 1 | 8 | 76 | 15 | 16 | 711 | 93.8% |
| | 2 | 8 | 76 | 15 | 16 | 711 | 93.8% |
| | 3 | 8 | 76 | 15 | 16 | 711 | 93.8% |
| | 4 | 8 | 76 | 15 | 16 | 711 | 93.8% |
| | 5 | 8 | 76 | 13 | 16 | 616 | 81.3% |
| | 6 | 8 | 76 | 12 | 16 | 568 | 75.0% |
| | 7 | 8 | 76 | 13 | 16 | 616 | 81.3% |
| | 8 | 8 | 76 | 13 | 16 | 616 | 81.3% |
| | 9 | 8 | 76 | 15 | 16 | 711 | 93.8% |
| | 10 | 8 | 76 | 13 | 16 | 616 | 81.3% |
| | 11 | 8 | 76 | 15 | 16 | 711 | 93.8% |
| | 12 | 8 | 76 | 15 | 16 | 711 | 93.8% |
| | 13 | 8 | 76 | 16 | 16 | 758 | 100.0% |
| | Overall | 104 | 988 | 185 | 208 | 674 | 88.9% |
| 3-Cuts | 1 | 8 | 97 | 22 | 24 | 816 | 91.7% |
| | 2 | 8 | 97 | 20 | 24 | 742 | 83.3% |
| | 3 | 8 | 97 | 19 | 24 | 705 | 79.2% |
| | 4 | 8 | 97 | 21 | 24 | 779 | 87.5% |
| | 5 | 8 | 97 | 16 | 24 | 594 | 66.7% |
| | 6 | 8 | 97 | 17 | 24 | 631 | 70.8% |
| | 7 | 8 | 97 | 18 | 24 | 668 | 75.0% |
| | 8 | 8 | 97 | 17 | 24 | 631 | 70.8% |
| | 9 | 8 | 97 | 22 | 24 | 816 | 91.7% |
| | 10 | 8 | 97 | 16 | 24 | 594 | 66.7% |
| | 11 | 8 | 97 | 20 | 24 | 742 | 83.3% |
| | 12 | 8 | 97 | 22 | 24 | 816 | 91.7% |
| | Overall | 96 | 1164 | 230 | 288 | 711 | 79.9% |
| 4-Cuts | 1 | 8 | 118 | 27 | 32 | 824 | 84.4% |
| | 2 | 8 | 118 | 25 | 32 | 763 | 78.1% |
| | 3 | 8 | 118 | 23 | 32 | 702 | 71.9% |
| | 4 | 8 | 118 | 26 | 32 | 793 | 81.3% |
| | 5 | 8 | 118 | 19 | 32 | 580 | 59.4% |
| | 6 | 8 | 118 | 22 | 32 | 671 | 68.8% |

TABLE I-continued

THE TEST RESULTS OF THE AUTOMATED MICROPROPAGATION
SYSTEM FOR VACCINIUM CORYMBOSUM - 'BILOXI'
WITH 2 CUTS, 3 CUTS, AND 4 CUTS.

| Test No. | No. of Available Shoots | Time [s] | No. of Successful Transplants | No of Ideal Transplants | Efficiency [shoots/hr] | Success Rate |
|---|---|---|---|---|---|---|
| 7 | 8 | 118 | 22 | 32 | 671 | 68.8% |
| 8 | 8 | 118 | 21 | 32 | 641 | 65.6% |
| Overall | 64 | 944 | 185 | 256 | 706 | 72.3% |

TABLE II

THE PERCENTAGE OF THE ERROR SOURCES WITH
RESPECT TO THE TOTAL NUMBER OF PLANTS
FOR 2 CUTS, 3 CUTS, AND 4 CUTS.

|  | 2-Cuts | 3-Cuts | 4-Cuts |
|---|---|---|---|
| Gripping Error | 7.7% (16/208) | 13.0% (30/230) | 14.1% (26/185) |
| Cutting Error | 1.0% (2/208) | 2.2% (5/230) | 1.6% (3/185) |

Based on the results of Table I, the success rate was greatly reduced as the number of cuts increased. This was mainly due to the alignment issue of the planting materials in the succeeding cuts. From Table II, the main error source for the 2-Cuts setting, the 3-Cuts setting, and the 4-Cuts setting all came from the gripping error, which, essentially, was resulted from the misalignment of the planting materials. During the first cut, the plantlets were perfectly aligned and therefore, all the plantlets were transferred to the new DVVs 22b successfully. However, in the successive cuts, some issues, such as insufficient gripping force due to uneven gripper surface, vibration due to the activation and deactivation of solenoid, etc. caused the plantlets to be slanted at an angle. Since the shoots were slanted, as the gripper moved up, the shoots became further away from the gripper. As a result, the gripper could not make contact with the shoots for successful consecutive cuts.

Besides the success rate, the efficiency is another evaluation parameter that was considered. JRT produces over a million blueberry plants every year and the estimated manual production rate is around 640 shoots per hour by cutting the plantlets into as many micro-shoots as possible. From Table I, the highest efficiency that the system achieved was around 711 shoots per hour with a success rate of 79.9% with 3-Cuts setting. Even though the success rate with 2-Cuts setting was higher, the efficiency was around 40 shoots lower hourly due to the reduced number of cuts. It showed that our approach of batch propagation is valid. The goal is to find the optimal number of plantlets for batch propagation while maintaining or improving the success rate. Research has shown that for an automated micropropagation system to be competitive, it has to produce at least 25% more than an average employee (i.e. the automated system 100 is expected to perform at 800 shoots per hour rate.

The efficiency is affected by two parameters: 1) the number of successfully planted shoots and 2) the time it took to process the plantlets. In order to increase the efficiency, one way was to increase the number of successfully planted shoots and the other way is to refine the algorithm and improve the processing time. Assuming the success rate remain the same, Table III shows the improvement over the efficiency if additional cells were added to the DVV 22. From Table III, it is observed that by increasing one addition cell in the DVV 22 for batch processing, the efficiency of the system improved 12.5% linearly. However, increasing the number of cells on the DVVs means that the size of the machine will become bigger. The goal is to find the optimal size of the DVV while maintaining a satisfactory efficiency. In this study, by adding one additional cell to the DVV 22 will allow the system to reach its desired efficiency, which is 800 shoots per hour.

TABLE III

THE IMPROVEMENT OVER EFFICIENCY IF ADDITIONAL
CELL(S) WERE ADDED TO THE DVV FOR 3-CUTS CONFIGURATION
ASSUMING THE SAME SUCCESS RATE.

| No. of Cells | No. of Tests | Available shoots | Supposed Total | Total Time [s] | Success Rate | Efficiency [shoots/hr] | Improvement in Efficiency |
|---|---|---|---|---|---|---|---|
| 9 | 12 | 108 | 324 | 1164 | 79.9% | 800 | 12.5% |
| 10 | 12 | 120 | 360 | 1164 | 79.9% | 889 | 25.0% |
| 11 | 12 | 132 | 396 | 1164 | 79.9% | 978 | 37.5% |
| 12 | 12 | 144 | 432 | 1164 | 79.9% | 1067 | 50.0% |

On the other hand, in order to compare the effectiveness of adding additional cell in the DVV 22 and reducing the processing time, Table IV shows the improvement over the efficiency if additional time were taken from each dissecting process for 3-Cuts setting. In the proposed system, the total amount of time it takes to complete one DVV consists of two portions: 1) the transporting time and 2) the processing time. To simplify the analysis, the transporting time, which is around 34 seconds, is kept constant, while the processing time, which is around 21 seconds, for each dissecting process is reduced. Assuming that the success rate and the size of the DVV remain the same, Table IV shows that the processing time for each cut has to be shortened by 3.6 second, which is a reduction of 17.1% of a single cut processing time, in order to achieve the same efficiency.

TABLE IV

THE IMPROVEMENT OVER EFFICIENCY IF ADDITIONAL TIME(S) WERE DEDUCTED FOR EACH CUT FOR 3-CUTS CONFIGURATION ASSUMING THE SAME SUCCESS RATE.

| Original Time [s] | Improved Processing Time [s] | % of Time Reduced | Efficiency [shoots/hr] | Improvement in Efficiency |
|---|---|---|---|---|
| 21 | 20 | 4.8% | 734 | 3.2% |
| 21 | 19 | 9.5% | 758 | 6.6% |
| 21 | 18 | 14.3% | 784 | 10.2% |
| 21 | 17.4 | 17.1% | 800 | 12.5% |
| 21 | 17 | 19.0% | 812 | 14.1% |

For testing purpose, the plantlets were set up manually. However, the system 100 can be designed so that the plantlets can be planted and grow in the DVVs so they can be loaded directly to the system 100 to minimize human contact. With the standardized dissecting and planting, the plantlets are more uniformly planted and result in higher success rate. With a 100% success rate and everything else remaining the same, the efficiency would reach 891 shoots per hour with 3-Cuts setting, which is a 39% increase over the current hourly industrial output.

In one implementation, the system 100 can be placed and work inside a laminar flow hood after it has been sterilized. In addition, the DVVs 22 can be manufactured with materials that withstand high pressure and high temperature. This allows the DVVs 22 to go through the standard autoclave sterilization procedure as currently utilized in the plant tissue culture laboratory.

Figure 8:
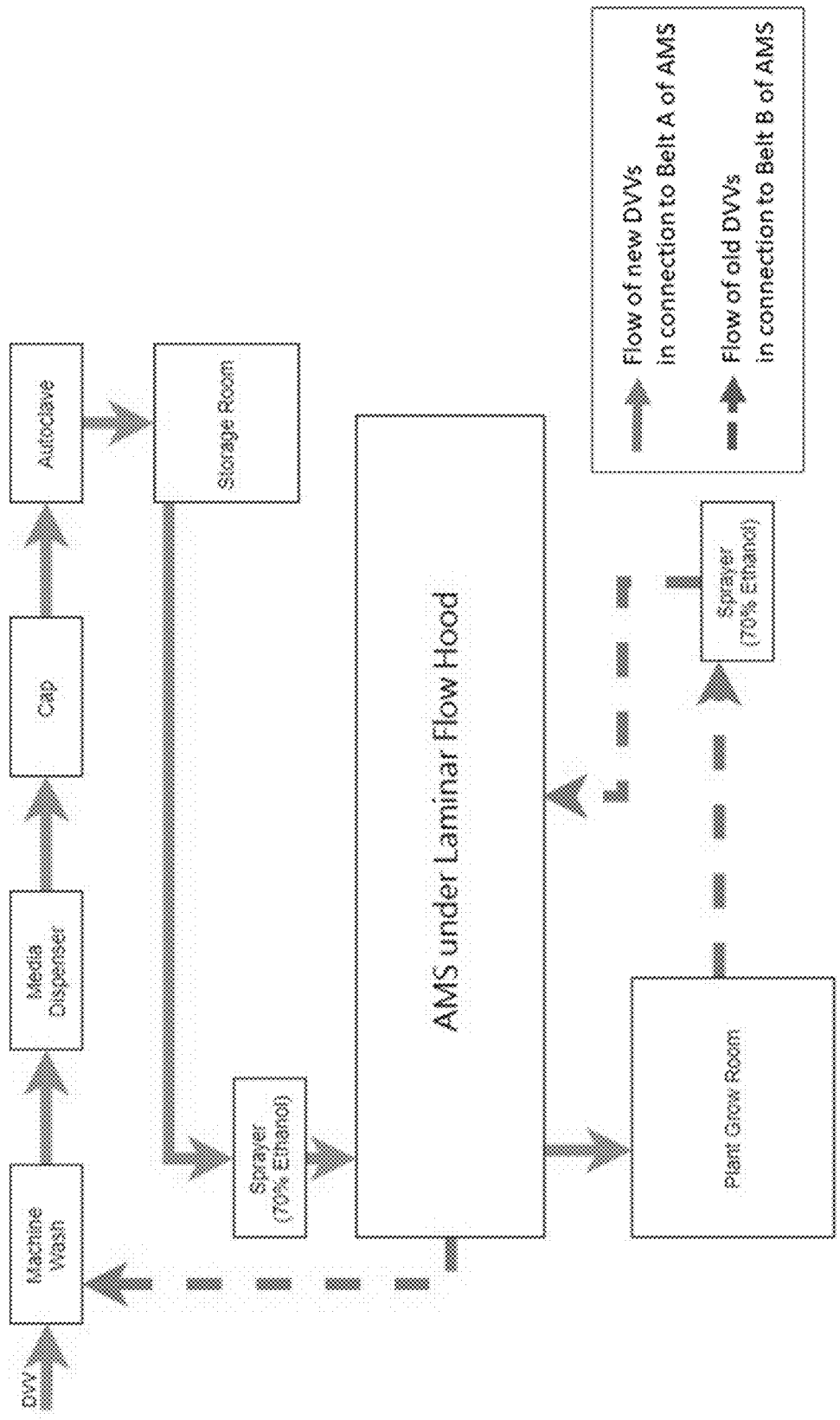
FIG. 8 is a flowchart of another example of an automated micropropagation process of the present invention.

FIG. 8 illustrates another mode of operation of the system 100. For example, the system 100 illustrated in FIG. 6 employs two assembly belts 106a and 106b. The belt 106b is used to carry the "new" DVVs 22b, while the other belt 106a is used to carry the "used" DVVs 22a. As shown in the FIG. 8, the new (or recycled) DVVs are washed with the washing machine and passed to the media dispenser, where the boiled media are added to the culture items. After that, the DVVs are stacked and enclosed together in arrays of four. They are then autoclaved and sent to the storage room until needed. When the automated micropropagation process starts, the new DVVs are brought under the laminar flow hood by placing them on belt 106b, whereas the used DVVs that contain the grown plantlets enter the hood through belt 106a. To maintain both DVVs under sterile condition, they are sprayed with 70% ethanol before entering the hood and the covers are removed. The newly planted DVVs on belt 106b are then capped and transferred to the plant grow room, whereas the processed old DVVs on belt 106a are recycled. In addition to the process described, a distilled water dispenser is mounted on top of the gripper and cutter assembly 40 to keep the assembly clean and free from plant residues every time for the transfer of explants to fresh solutions. In addition, the growing media can be modified so that the plantlets can grow straight up and without any cluster of buds. Also, liquid culture systems can be employed.

While particular elements, embodiments and applications of the present disclosure have been shown and described, it will be understood, that the scope of the disclosure is not limited thereto, since modifications can be made by those skilled in the art without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another or may be combined in various ways. All possible combinations and sub-combinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The example results and parameters of the embodiments described herein are intended to illustrate and not to limit the disclosed embodiments. Other embodiments can be configured and/or operated differently than the illustrative examples described herein.

The invention claimed is:

1. An automated micropropagation system for plant tissue culture to rapidly produce genetically identical plantlets, the system comprising:
   a culture vessel comprising a plurality of detachable vessel vectors (DVVs), each DVV comprising a plurality of individual and separated culture cells configured and sized to accept at least one plantlet per cell, wherein some of the DVVs are mother DVVs comprising at least one mother plantlet in each cell and some of the DVVs are new DVVs, where each of the cells in the new DVVs is filled with a growing medium;
   a plantlet feed-in assembly comprising a first feed-in driver in communication with at least one mother DVV of the mother DVVs and a second feed-in driver in communication with the new DVVs;

a motorized gripper and cutter assembly comprising a gripper, a cutter and an assembly driver that drives the gripper and the cutter in horizontal and vertical directions, the gripper having holders and a holders' driver to drive the holders into a closed and an opened position, when the holders are in closed position they securely hold an array of the plantlets simultaneously, the cutter comprising a shears driver in communication with a plurality of shears configured to cut the gripped plantlets to a predetermined length, the assembly driver configured to move the gripper between the mother and the new DVVs to transplant the dissected part of the plantlets into the new DVVs;

a collector assembly in communication with the gripper and cutter assembly is configured to collect the new DVVs containing the dissected parts and store them; and a controller configured to control the system, the controller being in communication with the first and second feed-in drivers, the assembly driver, the holder's driver and the shears' driver controlling the triggering time of each of the drivers independently.

2. The system according to claim 1, wherein any of the DVVs are adjusted to be stackable.

3. The system according to claim 1, wherein each of the individual culture cells has a closed bottom and a separation wall with associated thickness between each individual culture cells separating one individual culture cell from another.

4. The system according to claim 1, wherein the cutter dissects the plantlets transversally while the gripper holds the plantlets vertically with a nodal segment of each plantlet being in a natural position.

5. The system according to claim 1, wherein each of the holders comprises a pair of fingers, wherein when the pair of fingers are in closed position, a space between the gripper's fingers is pre-determined to fit a size of the plantlets accordingly.

6. The system according to claim 1, wherein the assembly driver drives the gripper and the cutter in horizontal and/or vertical directions independently one from another.

7. The system according to claim 1, wherein the mother DVVs are mounted manually to the feed-in assembly.

8. The system according to claim 1, wherein the first feed-in driver drives the mother DVV to the gripper and cutter assembly and the second feed-in driver drives the new DVV to the gripper and cutter assembly such that the mother DVV and the new DVV are positioned parallel one to another in horizontal direction.

9. The system according to claim 1, wherein the first feed-in driver and the second feed-in driver each comprise a motor and a conveyor belt.

10. The system according to claim 1, wherein the assembly driver comprises at least two linear actuators to drive the assembly in horizontal and vertical directions.

11. The system according to claim 1, wherein the new DVV are recycled used DVV, the used DVV being washed and sterilized before filled with the growing medium and mounted in the feed-in assembly as new DVVs.

12. The system according to claim 1, wherein the collector comprises a base to mount a collector tray, a linear actuator configured to mount the collector tray, a push plate to activate the linear actuator, and a light sensor to detect arrival of the new DVV.

13. The system according to claim 1, further comprising a plurality of sensors configured to provide input signals to the controller, the plurality of sensors detecting a position of the mother DVV and the new DVV in the system and sending an input signal of each change of DVVs position to the controller.

* * * * *